US00PP35215P2

(12) United States Plant Patent
Martinez et al.

(10) Patent No.: US PP35,215 P2
(45) Date of Patent: Jun. 13, 2023

(54) SEEDLESS TABLE GRAPEVINE NAMED 'ITUMTWELVE'

(50) Latin Name: *Vitis vinifera*
Varietal Denomination: Itumtwelve

(71) Applicant: Investigacion y Tecnologia de Uva de Mesa S.L., Blanca (ES)

(72) Inventors: Manuel Tornel Martinez, La Alberca (ES); Juan Carreno Espin, Murcia (ES)

(73) Assignee: Investigacion y Tecnologia de Uva de Mesa S.L.

( * ) Notice: Subject to any disclaimer, the term of this patent is extended or adjusted under 35 U.S.C. 154(b) by 0 days.

(21) Appl. No.: 17/990,842

(22) Filed: Nov. 21, 2022

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Cassandra Bright

(57) ABSTRACT

A new distinct variety of *Vitis vinifera* (Table grape) named 'Itumtwelve' forms distinctive seedless fruit with a black berry skin and a narrow ellipsoid berry shape. Fruit has a neutral flavor and a very firm flesh that together with a medium thickness of skin makes it crunchy at the first bite. Being a mid-season variety, the fruit commonly is ready for harvesting from August to mid-October in Murcia, Spain, and displays good eating qualities as a table grape. The fruit meatiness and firmness renders the fruit amenable for handling, shipping, and storage.

4 Drawing Sheets

Latin name of the genus and species: *Vitis vinifera*.
Variety denomination: 'ITUMTWELVE'.

BACKGROUND OF THE INVENTION

A breeding program was initiated during 2003 at a research nursery in Blanca, Murcia, Spain. During the development of this breeding program, a new variety of *Vitis vinifera* was created by deliberate cross breeding of two parent plants by emasculation of the pollen-bearing organ of the female and introducing pollen from another male origin. The female parent of the new variety is the unpatented variety 'Autumn Royal'. The male parent of the new variety is 'Crimson', unpatented.

'Itumtwelve' was identified as a potentially interesting selection during 2008 at the same location in Murcia, Spain. After identifying the new variety as a potentially interesting selection, first propagation of 'Itumtwelve' by vegetative cuttings was undertaken during 2009, at the same research nursery in Murcia, Spain. Controlled testing and propagation of the new variety continued over several years to assess stability of the unique characteristics of this variety. Subsequently, several generations have been reproduced and have shown that the unique features of this cultivar are stable and reproduced true to type. The first commercial sale of this new cultivar occurred Jan. 12, 2022. Plant material for this sale was obtained directly or indirectly from the inventor and occurred less than 1 year before filing of the U.S. plant patent application. This disclosure meets the requirement for exception under 35 USC 102(b)1.

SUMMARY OF THE INVENTION

The cultivar 'Itumtwelve' has not been observed under all possible environmental conditions. The phenotype may vary somewhat with variations in environment such as temperature, day length, and light intensity, without, however, any variance in genotype. These characteristics in combination distinguish 'Itumtwelve' as a new and distinct *Vitis* cultivar:

1. Very late individual berries with black skin coloration.
2. Attractive narrow ellipsoid berry shape.
3. As a mid-season variety, typically bears fruit for harvesting from August until mid-October in the region of Murcia, Spain.
4. Firm and crunchy berry texture.
5. Seedless fruit.
6. Fruit has been found to be suitable for handling and shipping.
7. Observed tolerance for drought.
8. Resistance to cracking.

COMPARISON TO PARENT VARIETIES

TABLE 1

| Characteristic | 'Itumtwelve' | |
|---|---|---|
| | | Parental A (fem) 'Autumn Royal' |
| Berry Texture | Very firm | Medium firmness |
| Berry Shape | Narrow ellipsoid | Ovoid |
| | | Parental B (masc.) 'Crimson' |
| Berry Skin Color: | Black | Red |
| Mature leaf arrangement of lobes of petiole sinus | Slightly Open | Slightly Overlapped |
| Berry Shape: | Narrow ellipsoid | Short elliptical |

COMMERCIAL COMPARISON

TABLE 2

| Characteristic | 'Itumtwelve' | |
|---|---|---|
| | | 'Itumtwo' (unpatented) |
| Mature leaf: proportion of main veins on upper side of blade with anthocyanin coloration | Low | High |
| Time of Berry Ripening | Mid-Season | Very Early |
| Berry Shape | Narrow ellipsoid | Obtuse ovoid |
| Mature leaf arrangement of lobes of petiole sinus | Slightly open | Half open |
| | | 'Superior' (unpatented) |
| Berry Shape | Narrow ellipsoid | Globose |
| Presence of Seeds | Absent | Complete |

BRIEF DESCRIPTION OF THE PHOTOGRAPHS

The accompanying photographic illustrations show typical samples of vegetative growth and fruit on a 9 year old specimen of the new variety, in color as nearly true as it is reasonably possible to make in a color illustration of this character. Plants were grown in Murcia, Spain. Colors in the photograph may differ from the color values cited in the detailed botanical description below, which accurately describes the colors of the new Grapevine.

DETAILED BOTANICAL DESCRIPTION

Figure 1:
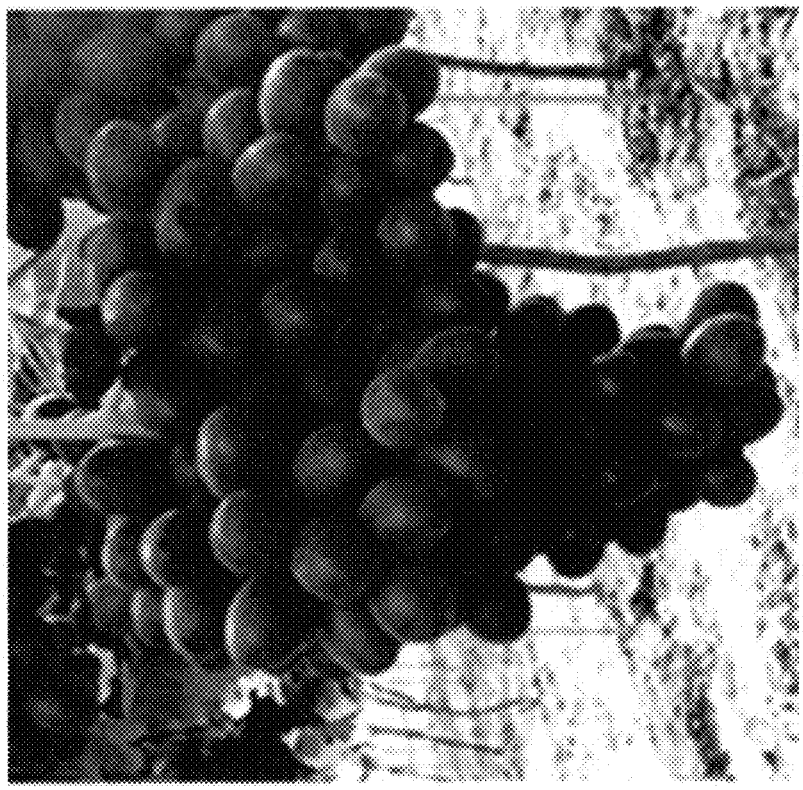
FIG. 1 illustrates a fruit cluster of 'Itumtwelve'.
Figure 2:
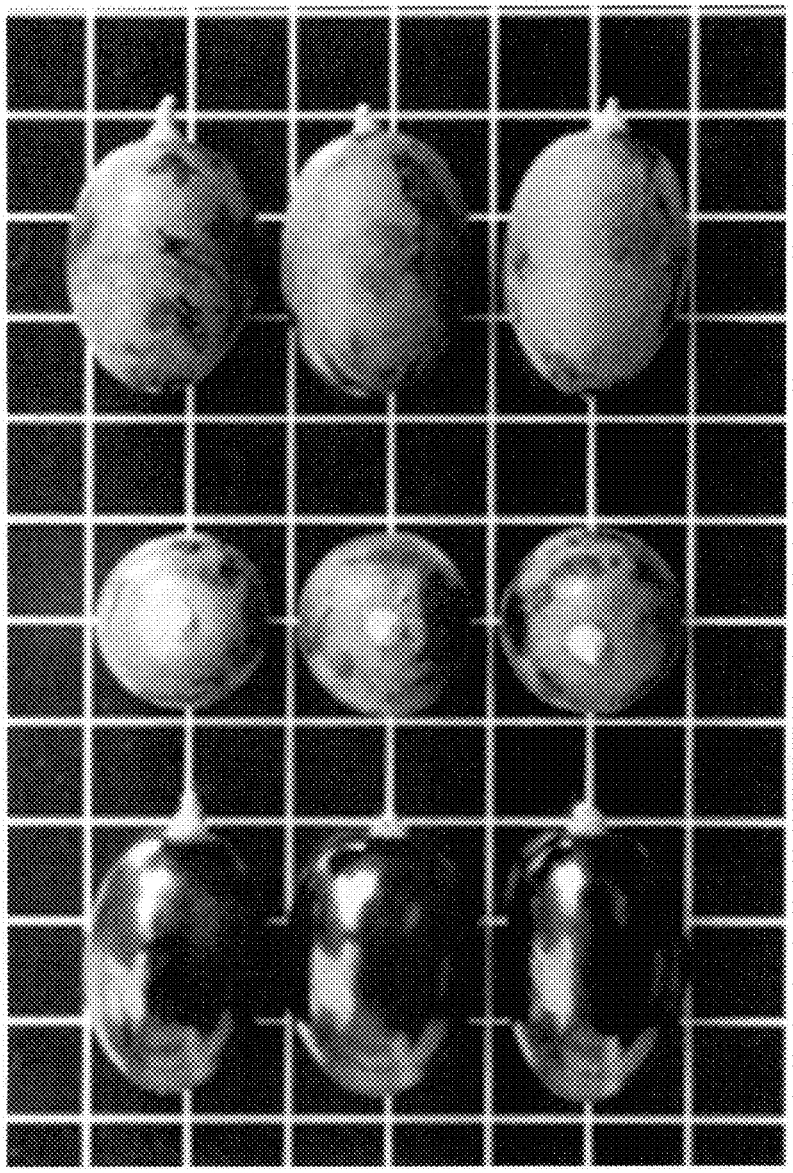
FIG. 2 shows a close-up view of individual berries of 'Itumtwelve'.
Figure 3:
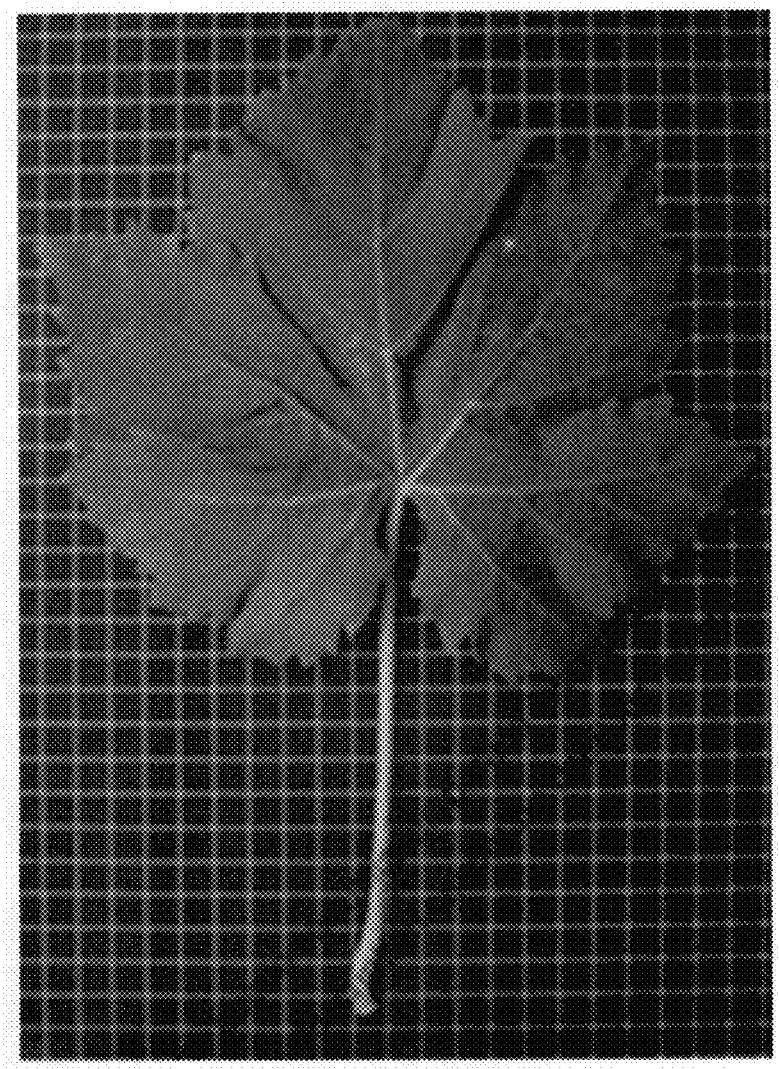
FIG. 3 illustrates in close up perspective typical foliage of the new variety.
Figure 4:
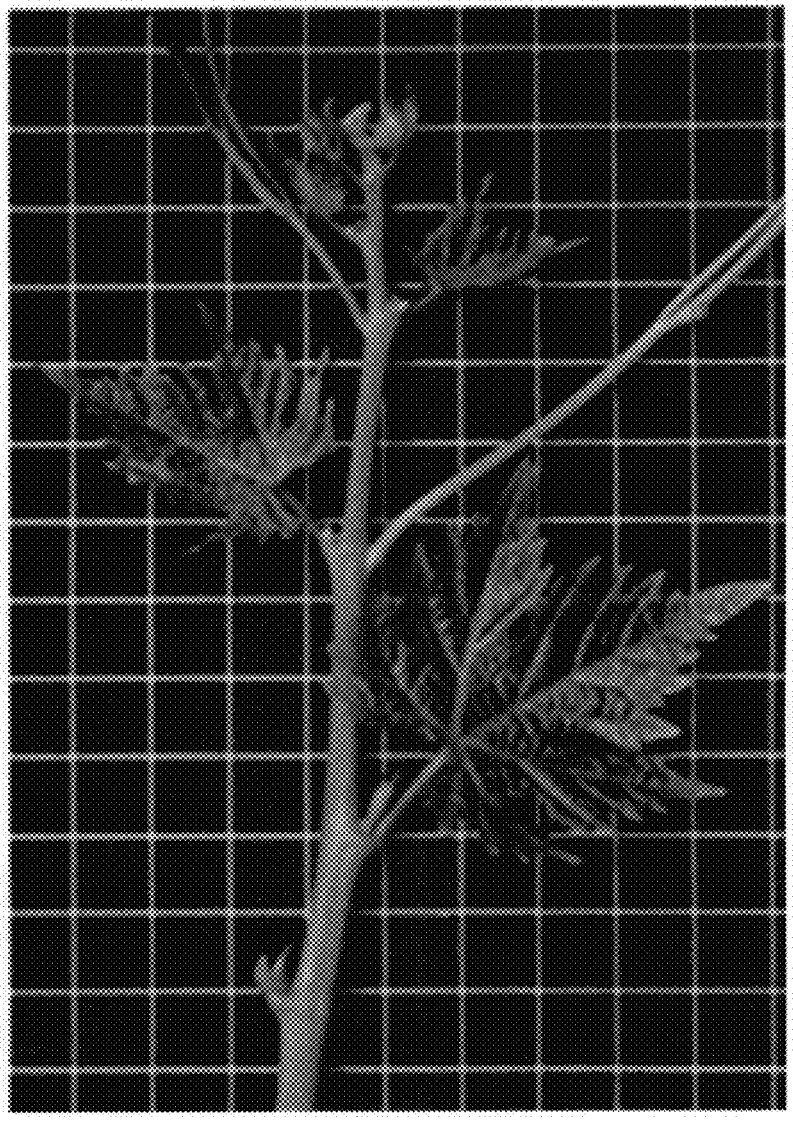
FIG. 4 illustrates a new shoot of 'Itumtwelve'.

In the following description, color references are made to The Royal Horticultural Society Colour Chart 2015 except where general terms of ordinary dictionary significance are used. Some descriptors, when useful have been incorporated from *UPOV Grape Descriptor Guidelines*. The description is based on the observation of plants growing on '1103 Paulsen' (not patented) rootstock in clay stony soil conditions in the fields near Blanca, Murcia, Spain. The age of plant described is 9 years old, with an average height of 200 cm, a high canopy density, a 300 cm plant spread, a one-year growth rate to reach two meters high and 20 to 30 days to initiate roots at approx. 20° C. At observation location temperature ranged between 15° C. to 35° C. during the day, and between 5° C. to 20° C. during the night.

Botanical classification: *Vitis vinifera* 'Itumtwelve'.

CANES

Characteristics of mature canes:
- *Diameter.*—1.2 to 1.6 cm.
- *Length.*—70 to 80 cm.
- *Color.*—Near RHS Greyed-Orange 164C.
- *Cross section shape.*—Circle.
- *Strength.*—Weak.
- *Texture.*—Non-pubescent, rough.

Lenticels:
- *Diameter.*—Less than 0.5 mm.
- *Density.*—Few to-moderate.
- *Color.*—Near RHS Greyed-Orange 164C.

Internode length: 8-12 cm.
- *Pigmentation at internode, dorsal.*—Near RHS Greyed-Orange 164C.
- *Pigmentation at internode, ventral.*—Near RHS Greyed-Orange 164C.

Tendril pattern on show: 0,0,0,0,1 or 0,0,0,0,0,1.
- *Tendrils forked.*—Yes.
- *Tendril texture.*—Glabrous.
- *Tendril length.*—6 to 12 cm.

Bud:
- *Bud width.*—0.8 to 1 cm.
- *Bud length.*—0.4 cm.
- *Bud shape.*—Deltoid.
- *Bud color.*—Near RHS Greyed-Yellow 161D, flushed 162D.

Young shoot:
- *Openness of tip.*—Open.
- *Anthocyanin.*—Not present in Shoot pigmentation.
- *Texture.*—Smooth.
- *Diameter.*—0.8 to 1.1 cm.
- *Longitudinal length.*—1.0 to 4.0 m; average 1.2 m.
- *Color.*—Near RHS Greyed-Orange 164D, streaked 165D.
- *Cross section.*—Circular.
- *Strength.*—Moderate.
- *Attitude.*—Semi-erect.
- *Bark texture.*—Shaggy.
- *Bark color.*—Near RHS Greyed-Red 179A streaked 180B.

FOLIAGE

Leaf:
- *Arrangement.*—Alternate.
- *Quantity.*—Approximately 15 per cane.
- *Average length.*—22 cm.
- *Average width.*—18 cm.
- *Overall shape of blade.*—Orbicular.
- *Apex.*—Acute.
- *Base.*—Cordate, overall rounded.
- *Margin.*—Dentate, teeth approximately 5 to 19 mm in length. Ratio of length to width about 1:1. Both sides of teeth straight or slightly convex one side.
- *Texture of top surface.*—Smooth.
- *Texture of bottom surface.*—Smooth.
- *Pubescence.*—None.
- *Aspect.*—Slightly undulate.
- *Lobes.*—3 to 5 slightly overlapping lobes.

Sinuses:
- *Shape of petiolar sinus.*—High widened.
- *Shape of base petiolar sinus.*—High widened.
- *Depth of petiolar sinus.*—5 cm.

*Width of petiolar sinus.*—2.6 cm.
*Shape of upper sinuses.*—High widened.

Color:
*Immature foliage upper side.*—Near RHS Yellow-Green 154D streaked 150D.
*Immature foliage under side.*—Near RHS Yellow-Green 154D streaked 150D.
*Mature foliage upper side.*—Near RHS Green 137A.
*Mature foliage under side.*—Near RHS Yellow-Green 144A.

Venation: Type: pinnate.
*Venation color upper side.*—Near RHS Yellow-Green 154C, anthocyanin coloration not observed.
*Venation color under side.*—Near RHS Yellow-Green 154C, anthocyanin coloration not observed.

Petiole:
*Length.*—16 cm.
*Diameter.*—0.3 cm.
*Color.*—Near RHS Yellow-Green 144A with weak Anthocyanin presence near base, Red 36C.
*Texture.*—Rough.

FLOWER

Flowering period begins around May 1 to 7 in Murcia, Spain.

Inflorescence when in bud:
*Length.*—9 cm.
*Diameter.*—4 cm.
*Bud color.*—Near RHS Green 140B.
*Bud shape.*—Conical.
*Bud size.*—About 1 to 2 mm by 1 to 2 mm.

Individual flower:
*Size of entire flower (to end of stamens).*—7 mm.
*Calyx shape.*—Funnel.
*Calyx size.*—15 mm.
*Calyx color.*—Near RHS Green 140B.
*Calyx apex.*—Rounded.
*Calyx base.*—Rounded.
*Calyx texture.*—Glabrous all surfaces.
*Diameter.*—12 mm.
*Quantity per flowering stem.*—5.
*Days lasting on plant.*—7 days.

Petals:
*Quantity.*—5.
*Arrangement.*—Symmetrical rotate.
*Length.*—0.17 cm.
*Width.*—<0.1 cm.
*Shape.*—Obovate.
*Apex.*—Ovate.
*Base.*—Ovate.
*Texture.*—Upper and lower surfaces glabrous and soft.
*Color.*—At opening upper surface: Near RHS Green 140B. At opening lower surface: Near RHS Green 140B. Fully opened upper Surface: Near RHS Green 140B.

Peduncles:
*Fruit peduncle length.*—55 mm.
*Fruit peduncle width.*—6 mm.
*Angle.*—About 70° to the lateral branch.
*Fruit peduncle strength.*—Firm.
*Fruit peduncle texture.*—Soft.
*Color.*—Near RHS Green 142D.

Pedicels:
*Length.*—4 mm.
*Diameter.*—0.5 mm.
*Angle.*—About 70° to center of flower cluster.
*Strength.*—Medium.
*Texture.*—Softly pubescent.
*Color.*—Near RHS Green 141C.

Fragrance: Absent.

REPRODUCTIVE ORGANS

*Number of Stamens.*—5.
*Anthers.*—Shape: oblong. Length: Approximately 1 mm. Color: Near Yellow 9C mixed with 10A.
*Pollen.*—Color: Near Yellow 7D mixed with 8A.
*Quantity.*—Abundant.
*Pistil Quantity.*—1. Length; 2.5 mm.
*Style.*—Length.—0.5 mm. Color: Near RHS Green 143C.
*Stigma.*—Shape: Round. Color: Near RHS Yellow-Green 144D.
*Ovary Color.*—Near RHS Yellow-Green 144D.

FRUIT

Cluster:
*Average length.*—20 cm.
*Average diameter.*—18 cm.
*Average weigh* 550 grams.
*Fertility index.*—number of clusters per sprouted buds: 1.

Fruit:
*Time of berry ripening.*—Mid-season variety, typically bears fruit for harvesting from August until mid-October in the region of Murcia, Spain.
*Average length.*—2.6 cm.
*Average diameter.*—1.9 cm.
*Shape.*—Narrow ellipsoid.
*Cross-section.*—Circular.
*Color of berry skin.*—Near RHS Black 202A.
*Color of berry flesh.*—Translucent, near White 155B.
*Brix at harvest.*—18.
*Ease of detachment from pedicle.*—Difficult, well hooked and difficult detachment.
*Thickness of skin.*—Medium.
*Firmness of flesh.*—Very crunchy and moderately firm.
*Particular flavor.*—Neutral to semi-acid.
*Fruit peduncle length.*—7.5 mm.
*Fruit peduncle width.*—5 mm.
*Fruit peduncle strength.*—Moderate.
*Fruit peduncle color.*—Near Green 143B and 143C.
*Formation of seeds.*—Not present.

OTHER CHARACTERISTICS

Disease and pest resistance: Not observed to be susceptible nor resistant to normal diseases and pests of *Vitis vinifera*.

Temperature tolerance: Observed growing between 6° C. to 42° C.

Drought tolerance: Observed to tolerate water shortages during the dry Summer months of Murcia, Spain without detriment.

What is claimed is:

1. A new and distinct cultivar of *Vitis* grapevine named 'Itumtwelve' as herein illustrated and described.

* * * * *